(12) United States Patent
Kuriger et al.

(10) Patent No.: US 12,029,849 B2
(45) Date of Patent: *Jul. 9, 2024

(54) BLOWER FOR BREATHING APPARATUS

(71) Applicant: Fisher & Paykel Healthcare Limited, Auckland (NZ)

(72) Inventors: Donald Roy Kuriger, Auckland (NZ); Johannes Nicolaas Bothma, Otorohanga (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 0 days.

This patent is subject to a terminal disclaimer.

(21) Appl. No.: 17/368,678

(22) Filed: Jul. 6, 2021

(65) Prior Publication Data

US 2021/0330909 A1 Oct. 28, 2021

Related U.S. Application Data

(63) Continuation of application No. 16/097,209, filed as application No. PCT/IB2017/052459 on Apr. 28, 2017, now Pat. No. 11,097,076.

(Continued)

(51) Int. Cl.
*A61M 16/00* (2006.01)
*F04D 25/06* (2006.01)
(Continued)

(52) U.S. Cl.
CPC ..... *A61M 16/0066* (2013.01); *F04D 25/0606* (2013.01); *F04D 29/053* (2013.01);
(Continued)

(58) Field of Classification Search
CPC ...... A61M 16/0066; A61M 2205/3606; A61M 2205/362; A61M 2205/42; F04D 25/0606;
(Continued)

(56) References Cited

U.S. PATENT DOCUMENTS

| 1,714,484 A | 5/1929 | Johnson |
| 3,711,218 A | 1/1973 | Omstein |

(Continued)

FOREIGN PATENT DOCUMENTS

| DE | 2206398 | 4/1974 |
| JP | 2004-183620 | 7/2004 |

(Continued)

OTHER PUBLICATIONS

International Search Report and Written Opinion for PCT Application PCT/IB2017/052459, mailed Jul. 14, 2017 in 13 pages.
(Continued)

*Primary Examiner* — Valerie L Woodward
*Assistant Examiner* — Paige Kathleen Bugg
(74) *Attorney, Agent, or Firm* — Knobbe Martens Olson & Bear LLP

(57) ABSTRACT

This invention relates to a blower for a breathing apparatus. The blower comprising a bottom support with a stub axle, a top support with a stub axle, a motor core comprising a motor stator and rotor, and an impeller coupled to the motor core via a shaft, the shaft is rotatably coupled at a first end to the stub axle on the top support and at a second end via the stub axle on the bottom support.

19 Claims, 15 Drawing Sheets

Related U.S. Application Data

(60) Provisional application No. 62/329,450, filed on Apr. 29, 2016.

(51) Int. Cl.
  *F04D 29/053* (2006.01)
  *F04D 29/059* (2006.01)
  *F04D 29/42* (2006.01)
  *F04D 29/58* (2006.01)

(52) U.S. Cl.
  CPC ....... *F04D 29/059* (2013.01); *F04D 29/4253* (2013.01); *F04D 29/5806* (2013.01); *A61M 2205/3606* (2013.01); *A61M 2205/362* (2013.01); *A61M 2205/42* (2013.01)

(58) Field of Classification Search
  CPC .. F04D 29/053; F04D 29/059; F04D 29/4253; F04D 29/5806; F04D 17/16; F04D 17/165
  USPC ..................................... 128/204.21
  See application file for complete search history.

(56) References Cited

U.S. PATENT DOCUMENTS

| | | | |
|---|---|---|---|
| 6,386,839 | B1 | 5/2002 | Chuang |
| 11,097,076 | B2 | 8/2021 | Kuriger et al. |
| 2004/0108779 | A1 | 6/2004 | Boettger et al. |
| 2005/0260073 | A1 | 11/2005 | Hsu et al. |
| 2005/0265834 | A1 | 12/2005 | Wang et al. |
| 2007/0020128 | A1* | 1/2007 | Chang ................... F04D 19/007 417/423.5 |
| 2007/0252460 | A1 | 11/2007 | Cheng |
| 2008/0304986 | A1* | 12/2008 | Kenyon ................ F04D 25/08 417/423.12 |
| 2013/0170943 | A1* | 7/2013 | Jonsson ................ F04D 29/058 415/1 |
| 2014/0216460 | A1* | 8/2014 | Bothma .............. F04D 29/5806 128/204.18 |
| 2014/0314592 | A1* | 10/2014 | Keon ..................... F04D 29/30 417/423.14 |
| 2014/0341759 | A1* | 11/2014 | Calico .................... F04D 25/02 417/349 |
| 2015/0328418 | A1* | 11/2015 | Bothma .............. F04D 25/0606 128/204.19 |
| 2016/0114121 | A1* | 4/2016 | Holley .............. A61M 16/0066 128/205.12 |
| 2016/0199612 | A1* | 7/2016 | Foote ................ A61M 16/0875 128/202.27 |
| 2016/0243325 | A1* | 8/2016 | Bowman ........... A61M 16/0069 |
| 2019/0134329 | A1 | 5/2019 | Kuriger et al. |
| 2021/0180602 | A1* | 6/2021 | Aynsley ................ F04D 25/088 |

FOREIGN PATENT DOCUMENTS

| | | |
|---|---|---|
| JP | 2012-152094 A | 8/2012 |
| JP | 2015-506253 A | 3/2015 |
| KR | 10-2011-0044416 | 2/2013 |
| WO | WO 2011/049279 | 4/2011 |
| WO | WO 2014/210093 | 12/2014 |
| WO | WO 2017/187392 | 11/2017 |

OTHER PUBLICATIONS

Chinese First Office Action with English Translation for Application No. 201780039676.3 dated Nov. 3, 2020, 19 pages.
European Extended Search Report for Application No. 17788928.4 dated Nov. 15, 2019, 6 pages.
Japanese Exam Report for Application No. 2018-556831 dated Mar. 25, 2021, 3 pages.

* cited by examiner

BLOWER FOR BREATHING APPARATUS

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

BACKGROUND

Field of the Invention

The present invention relates to a reduced foot-print blower, preferably for use in breathing apparatus such as CPAP breathing apparatus.

Background

Blowers are used in a range of breathing apparatus applications, and also other applications.

SUMMARY

It is an object of the present invention to provide a smaller blower. This enables the blower to be used in a range of applications where lower weight, inertia and/or size are desirable, such as in portable, body/head mounted and/or miniaturised breathing apparatus.

In one aspect the invention may comprise a blower for a breathing apparatus comprising: a bottom support with a stub axle, a top support with a stub axle, a motor core comprising a motor stator and rotor, an impeller coupled to the motor core via a shaft, wherein the shaft is rotatably coupled at a first end to the stub axle on the top support and at a second end via the stub axle on the bottom support.

Optionally the shaft is rotatably coupled at the first and second ends to the stub axles by bearings in the shaft.

Optionally the stub axle is compliant and/or resilient.

Optionally the shaft is partially or fully hollow and the first and second ends have bearings within the hollow.

Optionally each bearing comprises an inner race and an outer race, and each stub axle couples to the respective inner bearing race.

Optionally the shaft maximum diameter size is independent of the bearing diameter size.

Optionally the blower is an axial inlet/axial outlet blower.

Optionally the blower is a single stage axial inlet/axial outlet blower.

Optionally the impeller is integrally formed with the shaft or is coupled via a press-fit.

Optionally the rotor or magnet is press-fit on the shaft.

In another aspect the present invention may comprise a blower for a breathing apparatus comprising: a housing, a motor core within the housing, an impeller coupled to the rotor via a shaft, an airflow stator, wherein the impeller rotates within a region within the housing and directs outlet air axially through the airflow stator ring.

Optionally there is no volute.

Optionally the housing comprises a lower housing with a region for the motor and one or more apertures for axially receiving inlet air.

Optionally the blower is single stage.

Optionally the ratio of the impeller diameter to housing diameter is at least about 90%.

In another aspect the present invention may comprise a blower for a breathing apparatus comprising: a housing, a motor core within the housing, an impeller coupled to the rotor via a shaft, wherein the impeller comprises: a hub, blades extending from the hub, and stub blades supported between the blades.

Optionally an annular ring extending around the blades and supporting the stub blades.

Optionally the annular ring has an edge turned towards the outlet to direct outlet air axially.

Optionally the blower has:
a diameter of less than or equal to about 53 mm,
a height of less than or equal to about 21 mm, and/or
a weight of less than or equal to about 50 grams, or preferably less than or equal to 47 grams and preferably 27 grams.

Optionally the impeller has:
a thickness of less than or equal to about 3 mm
a diameter of less than or equal to about 48 mm, or more preferably 48.4 mm
a weight of less than or equal to about 3 grams Optionally the impeller is integrally formed with the shaft or is coupled via a press-fit.

Further aspects of the invention, which should be considered in all its novel aspects, will be described in the following description.

It should be noted that various changes and modifications to the presently preferred embodiments described herein will be apparent to those skilled in the art. Such changes and modifications may be made without departing from the spirit and scope of the apparatus and systems of the disclosure and without diminishing its attendant advantages. For instance, various components may be repositioned as desired. It is therefore intended that such changes and modifications be included within the scope of the apparatus and systems of the disclosure. Moreover, not all of the features, aspects and advantages are necessarily required to practice the present apparatus and systems of the disclosure. Accordingly, the scope of the present apparatus and systems of the disclosure is intended to be defined only by the claims that follow.

Reference to any prior art in this specification is not, and should not be taken as, an acknowledgement or any form of suggestion that that prior art forms part of the common general knowledge in the field of endeavour in any country in the world.

Wherein the foregoing description reference has been made to integers or components having known equivalents thereof, those integers are herein incorporated as if individually set forth.

Unless the context clearly requires otherwise, throughout the description and the claims, the words "comprise", "comprising", and the like, are to be construed in an inclusive sense as opposed to an exclusive or exhaustive sense, that is to say, in the sense of "including, but not limited to".

The apparatus and system of the disclosure may also be said broadly to consist in the parts, elements and features referred to or indicated in the specification of the application, individually or collectively, in any or all combinations of two or more of said parts, elements or features.

BRIEF DESCRIPTION OF THE DRAWINGS

Embodiments of a low profile blower will now be described with reference to the following drawings.

FIRST EMBODIMENT

Figure 1:
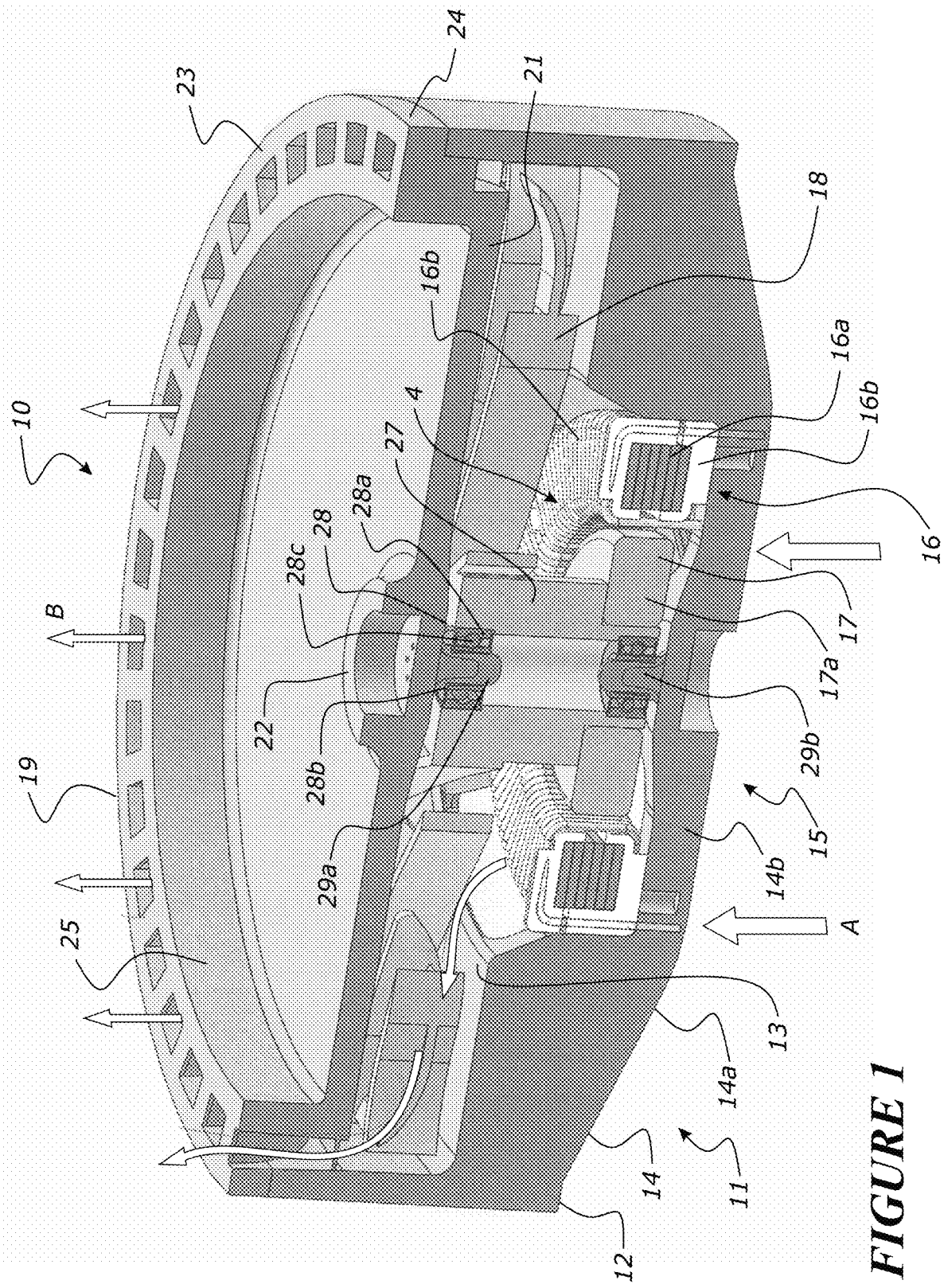
FIG. 1 shows a cross-sectional perspective view of a low-profile blower with an axial input and an axial output according to a first embodiment.
Figure 2:
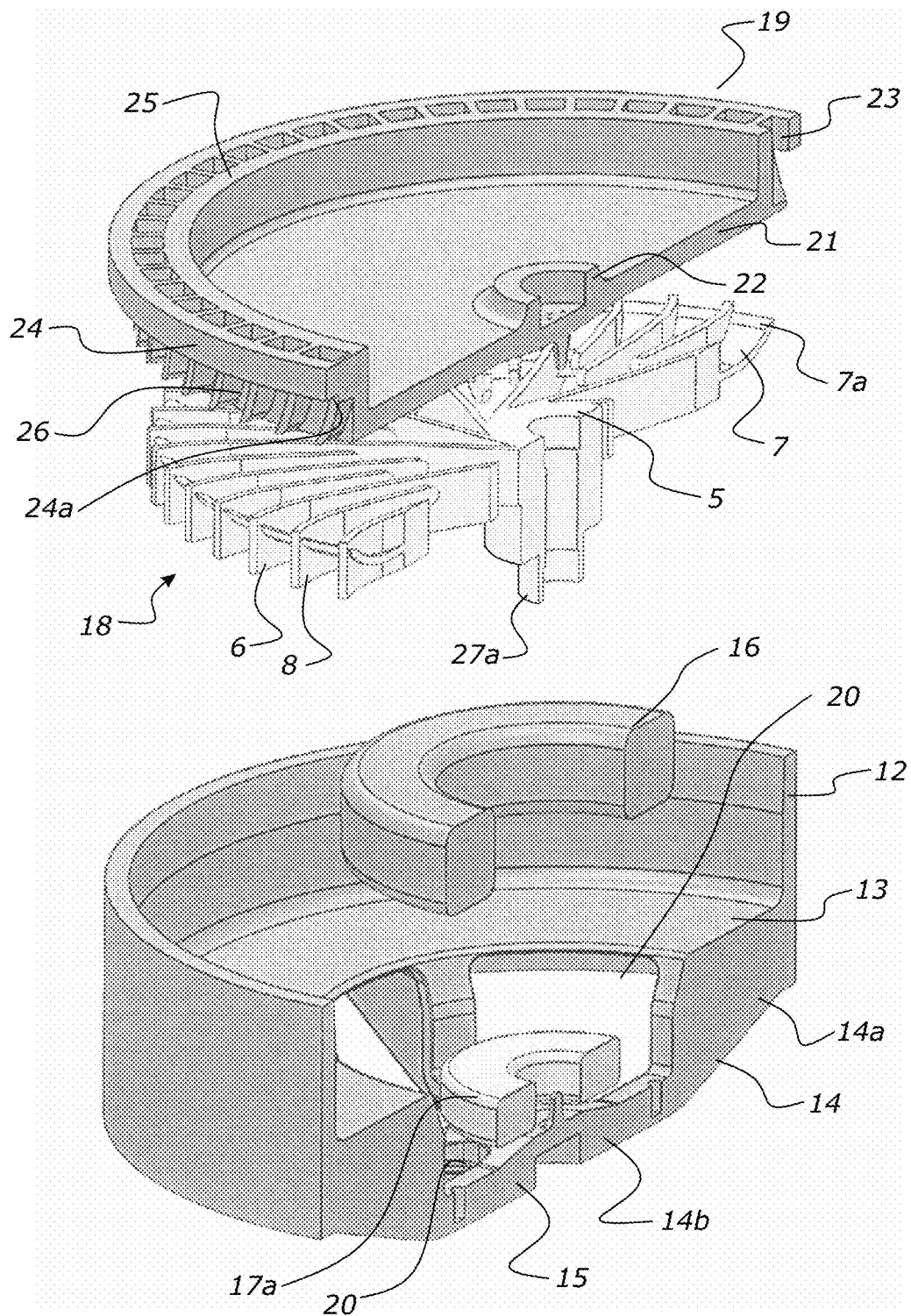
FIG. 2 shows a partial exploded view of the low-profile blower.

FIGS. 1 and 2 shows one embodiment of single-stage axial inlet/axial outlet blower (also called flow generator or fan). The low-profile blower is for use, for example, as a flow generator of a CPAP apparatus, high flow therapy apparatus or any other breathing apparatus. Alternatively, it can be used for any other suitable application.

The blower 10 comprises a bottom housing portion ("lower housing") 11. The lower housing is formed as an annular wall 12 with an internal annular shelf 13. Radial ribs 14 extend from the underneath from the annular shelf (or pan). The ribs are formed as wall portions 14a that have radial arms 14b extending from a lower portion that meet at a central (lower) hub 15. This forms a recessed region ("sub-housing") 20 (see FIG. 2) between the ribs 14, 13 annular shelf and the lower hub 15 for receiving a motor core 4 comprising a motor stator 16 and rotor 17. The lower housing 11/lower hub 15 act as a bottom/lower support for the motor stator 16, and at least a partial support for a bearing, which in turn provides support for the rotor 17 and an impeller 18 assembly. The apertures or gaps between ribs 14 provide an axial inlet for air flow "A". This provides motor cooling also.

The blower 10 also comprises a top housing portion ("upper housing") 19, which sits on the lower housing 11. The upper housing comprises a top plate 21 (internal lid) with a central boss forming an upper hub 22. An airflow ring 23 encircles the top plate. The airflow ring comprises an annular perimeter (outer annular wall) 24 with a rebate 24a (see FIG. 2) that sits on and couples to the top of the annular wall 12 of the lower housing 11; and an inner annular wall 25. This could be by way of bayonets, bumps, snap fits, glue, ultrasonic or friction welding, or any other suitable means. Curved channels e.g. 26 (see FIG. 2) are formed between the inner and outer annular walls for receiving and slowing airflow from the impeller 18 to create pressure. The upper housing acts as a top/upper support for the rotor and impeller assembly via a bearing 28.

Note, while the terms "upper", "lower", "top", "bottom" and the like are used throughout this specification, it will be appreciated that those terms are just relative terms used for referencing the drawings. The actual blower in use might be orientated differently, and so references to vertical positions herein should not be considered limiting, and should not be considered to refer to or limit the actual orientation of the blower and its components.

The motor core 4 comprises the motor stator 16 and rotor 17. The motor stator is supported on the radial arms 14b of the ribs 14 in the sub-housing 20. They could be friction fitted, over moulded or glued to the sub-housing 20, for example. The motor stator 16 comprises an annularly stacked laminated core 16a with a toroidal winding 16b. The rotor comprises a toroidal magnet 17a coupled to a shaft 27. The magnet could be coupled with a friction fit to the shaft, or coupled via over moulding or gluing. The lower end of the shaft 27 has an annular rebate 27a (see FIG. 2) with an external diameter commensurate with the inner diameter of the annular magnet 17a for receiving the annular magnet. The shaft 27 is a cylindrical tube in the form of a bearing tube. A bearing e.g. 28 is disposed in the bearing tube at each end. The bearing can have a friction fit with the shaft 27, or can be coupled via over moulding or gluing. Reference numerals refer to the top bearing 28, but these are equally applicable to the bottom bearing. Each bearing race comprises an outer annular bearing race/housing 28a, an inner annular bearing race/housing 28b and ball or roller bearings 28c movable therebetween in a cage. As one non-limiting example, the bearings can have an outside diameter of about 4 mm to 8 mm, an inside diameter of about 1.5 mm to 3 mm and a thickness of about 2 mm to 4 mm. The outer bearing race 28a rotates relative to the inner bearing race 28b. The inner bearing race can remain stationary. In alternatives, a plane bearing or bushing could be used instead. The shaft 27 is simply supported between the upper housing 19 and the lower housing 11. Both the upper housing and the lower housing comprise stub axles 29a, 29b in the form of compliant and/or resilient protrusions that extend into and couple to the bearing races 28a, 28b of the respective bearings at each end of the shaft. Preferably, the stub axles could be solid and/or rigid and are over moulded with a resilient and/or flexible material, such as silicone. Alternatively, the stub axles are formed from an elastomer (e.g. silicone) or other compliant and/or resilient material, and have a friction fit within the respective bearing races. Alternatively, the stub axles could be solid.

Each of the stub axles extend to a distal end from respective upper and lower housings. The stub axles extend towards each other. Each of the stub axles are substantially cylindrically shaped. In other embodiments, one or both of the stub axles taper or decrease in diameter as they extend away from their respective upper and lower housings. The distal end of each stub axle is rounded. However, in other embodiments, the distal end of one or both of the stub axles is substantially flat. Each stub axle also comprises a shoulder that is formed by a flange or stepped portion. In other embodiments, the shoulder formed by a taper in the stub axle. The shoulder is located at or near a proximal end of each stub axle to the respective housing from which it extends. Upper and lower bearings engage the shoulder or respective stub axles to limit axial movement of the bearing arrangement away from the shaft. The shaft also has a shoulder formed at each end in an opposed relationship to each respective stub axle shoulder. Each shaft shoulder is formed as a recess or stepped portion in an internal surface of the shaft. In other embodiments, the shaft shoulder is formed by a taper in the internal surface of the shaft. The upper and lower bearings also engage respective shaft shoulders so that they are gripped between a shoulder on the shaft and a shoulder on a stub axle. The shaft/stub axle/bearing arrangement enables the shaft to be rotatably supported/coupled in a simply supported manner to the upper/lower housing.

The outer diameter of the outer bearing race 28a could be about 4 mm, for example. The hollow shaft could have a commensurate diameter of about 4 mm to allow for a snug fit of the bearing race 28a. The outer shaft size in the rebate 27a could be about 5 mm.

Figure 5:
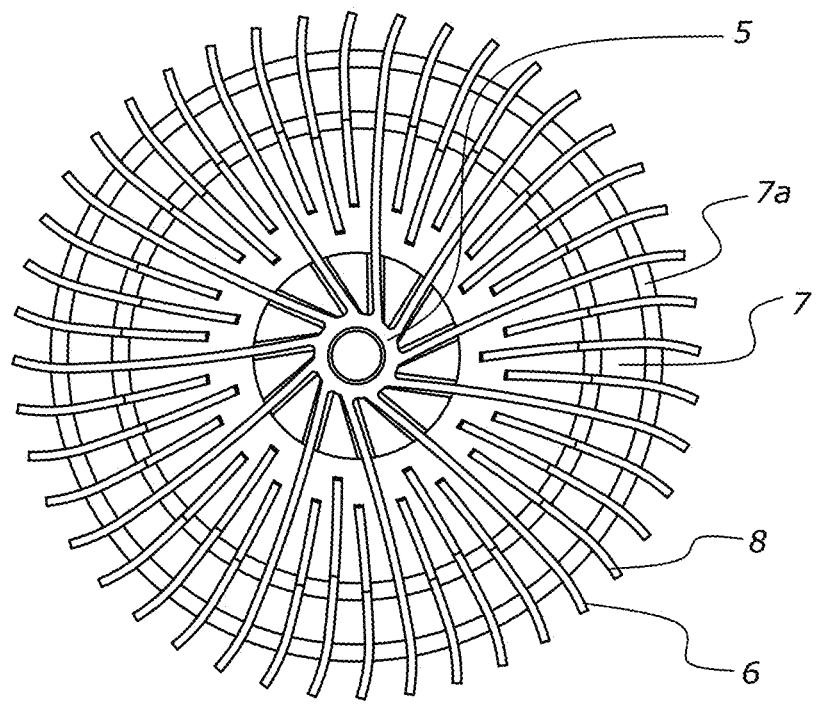
FIGS. 5 and 6 show another embodiment of an impeller that can be used with any of the previous embodiments.
Figure 6:
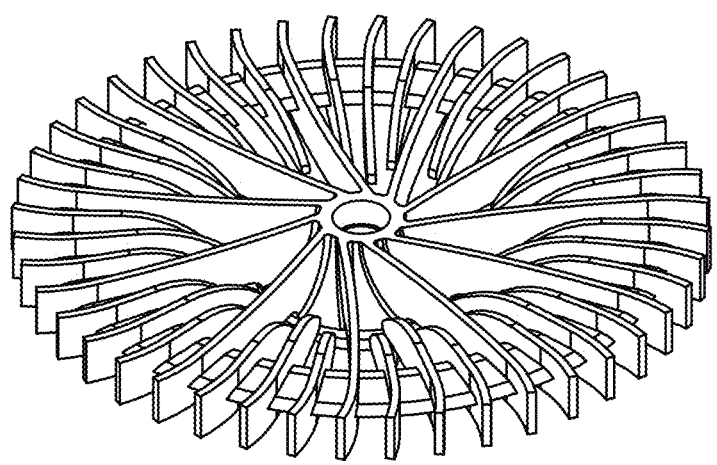

The impeller 18 can be coupled onto (e.g. press fit) or integrally formed with the shaft 27, or integrally formed or over moulded or glued onto the shaft. The impeller is shown in FIG. 2. The shaft can be of similar diameter to the shaft in traditional topologies, which allows for robust mechanical coupling of the impeller and the magnet. Because the bearings are fitted on the inside of the shaft, the diameter of the shaft is not dictated by the inner diameter of the bearings. The outer diameter of the shaft can then be a suitable size to allow for a robust impeller coupling, e.g. about 5 mm, or alternatively from about 3 mm to about 5 mm. A larger diameter shaft can still be used without dictating the bearing diameter size, because the bearings are internal to the shaft, the size of the bearing (e.g. the diameter size) can be selected based on acceptable bearing speed. For example, a smaller bearing can be used which is capable of higher RPM because the diameter is smaller and therefore the balls are not moving in the race as quickly as they would be for a large bearing. Using a smaller bearing enables higher RPM because smaller bearings are generally rated for higher RPM. The impeller is shown in FIG. 2. The impeller is also shown in FIGS. 5 and 6 in more detail. Similarly, the magnet/rotor 17a/17 is pressed onto the shaft. Similar advantages apply here, where the shaft can be a suitable size to allow for robust coupling. The impeller 18 comprises a hub portion 5 and flat forward swept (full-length) blades (sometimes called "vanes") 6, which radially extend from and connect to the hub portion. (Alternatively, the blades could be backward swept or radial). Each blade comprises a vertical flat portion extending from the hub. An annular rib/ring 7 is formed into the blades 6 and extends between them to provide rigidity at the perimeter of the blades. The ring curves towards the outlet 7a to provide rigidity to the blades and also direct airflow through the airflow stator to be described later. A plurality of short stub (partial-length) blades 8 (also termed "splitter blades") that extend part-way to the hub are interspaced between the full length blades 6. Each of the stub blades are also forward swept in the illustrated embodiment. The annular rib 7 is formed into and extends between the stub blades 8, thus supporting them. The stub blades provide additional pressure normally achieved with additional blades, without the requirement for material to extend to the hub which reduces air space at the hub. Reducing airspace at hub reduces the maximum flow capability of the blower 10. If the number of blades is too high (and therefore there is too little air space at the hub due to too many blades), inlet flow is occluded, which restricts the outlet airflow of the blower.

In the impeller as shown in FIGS. 5 and 6 there are three stub blades between each pair of full length blades 6. However, it will be appreciated that other numbers of sub blades 8 are possible. For example there may be between 1 and 7 stub blades or between 3 and 5 stub blades, or 1, 2, 3, 4 or 5 stub blades. In the illustrated embodiments of FIGS. 3 and 5, the stub blades 8 are of different lengths. A middle or intermediate stub blade of each group of stub blades between adjacent full length blades is longer than the adjacent stub blades (i.e. the stub blades to either side of the middle stub blade of that group of stub blades). The side stub blades are of approximately the same length. Despite the different lengths, peripheral ends of all of the stub blades in each group are disposed the same distance radially around the impellor. This means that the interior end of the longer, middle stub blade is disposed radially closer to the centre of the impellor than the interior end of each of the side stub blades. Peripheral ends of all of the stub blades and the full length blades are also disposed the same distance radially around the impellor. Each of the stub blades are tapered towards their interior ends. That is, each of the stub blades reduces in height towards their interior ends. To achieve this taper each of the stub blades has a convex top edge. Hence, each of the stub blades are narrower at their interior ends relative to their peripheral ends.

Material properties and construction techniques dictate that it is advantageous to increase the blade count when pumping liquids because of their higher density. For example, the rotation rate (Hz) is multiplied by the number of blades to determine the blade pass frequency. Human hearing is sensitive to tonal inputs between 300 Hz and 15 kHz and if not melodious, it is classified as noise. High frequency sound waves are easier to attenuate than low frequency noise. Typical CPAP blowers have rotational speeds of around 180 revolutions per second. It is therefore advantageous to increase the blade count to improve attenuation characteristics. Unequal, dissimilar and prime numbers like 7, 11, 13, 17, 19 and 23 help to reduce common fraction interactions between rotor and motor stator. As another example, decelerating a fluid by increasing the flow area rapidly can result in boundary layer separation, flow reversals and turbulent losses. Pressure loss recovery via diffusion mechanisms dictate that the angle between blades should not exceed 12 degrees. Dividing the full circumference (360 Degrees) by the sum of the blade thickness angle and the flow channel angle, a minimum blade number for optimal diffusion can be calculated. Adding more blades than optimal reduces the flow channel size with an increase in pressure drop.

But, increasing the blade count to distribute the force that a single blade has to support and to aid noise reduction decreases the size of the flow channel through the impeller, which is disadvantageous. The present inventors have overcome this issue by using stub/splitter blades. To minimise occlusion closer to the hub some blades may be truncated, referred to as splitter blades. Splitter blades could be placed on a support disc or shrouds to transfer their part of the load to the hub. But, blisks (bladed disks) and shrouded impellers have much higher rotational inertia. The present inventors have avoided this by supporting the splitter blades on a rib 7 as described, which reduces inertia over a shroud or disc, and also minimises occlusion.

The motor is controlled using a power supply and a controller to rotate the impeller to create the desired output air flow (both pressure and/or flow rate). Air is drawn through the apertures in the axial inlet by way of the impeller, over the motor to provide cooling, and directed to the air flow stator via the impeller blades and ring. The air flow stator ring slows the flow to create pressure, and the flow is directed axially out the airflow stator ring.

SECOND EMBODIMENT

Figure 3:
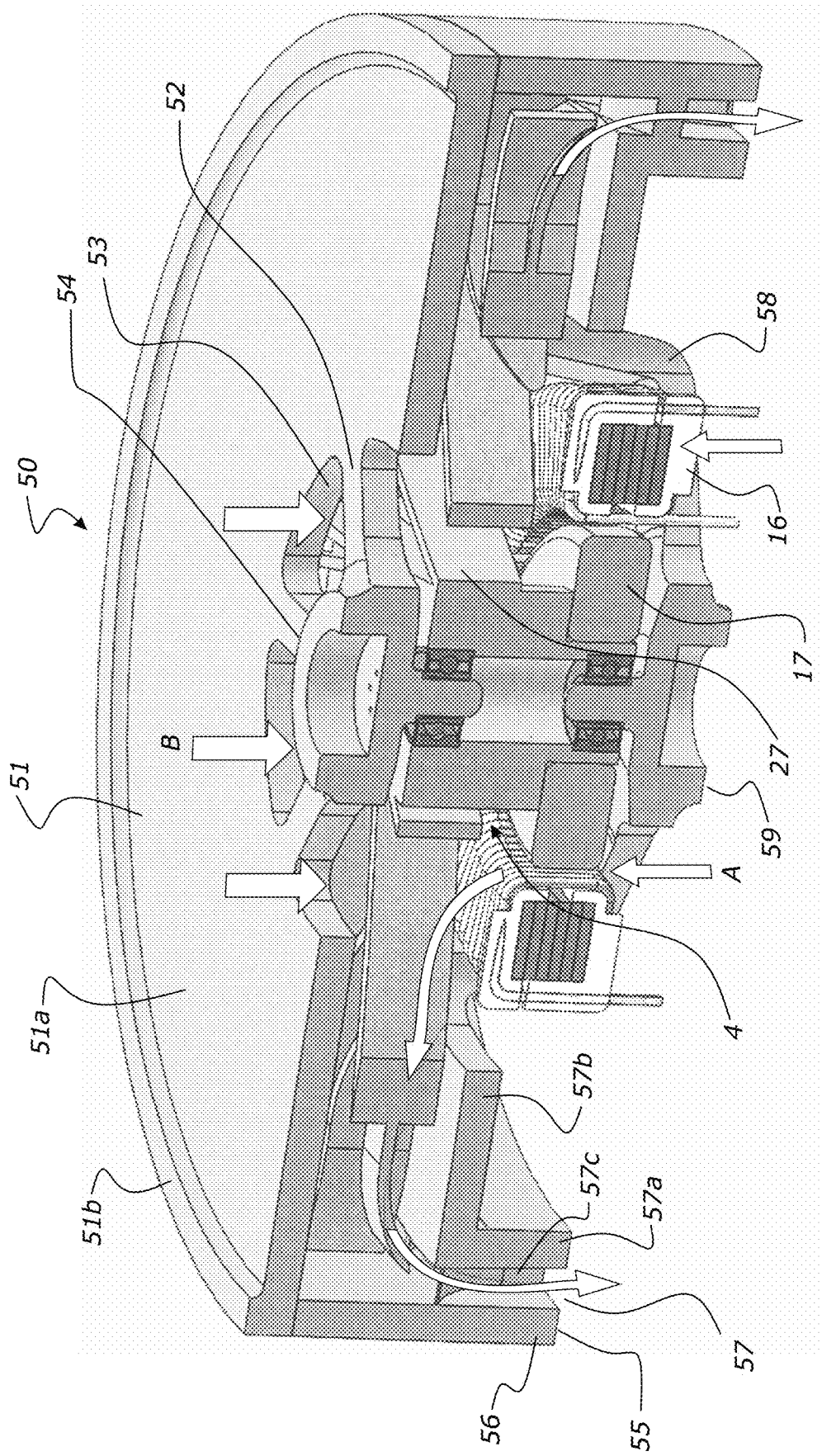
FIG. 3 shows a cross-sectional perspective view of a low-profile blower, with two axial inlets and an axial output according to a second embodiment.

FIG. 3 shows another embodiment of a single-stage axial inlet/axial outlet blower. In this embodiment, there are two axial inlets, one at the top of the motor and one at the bottom. Two inlets allows for a smaller inlet, which in turn allows for more effective blade length. There is also less noise associated with a smaller inlet.

The blower 50 comprises a top housing portion ("upper housing") 51 comprising a plate 51a with an annular rim 51*b*. At a central portion of the plate, a plurality of radial ribs 52 extend into a central (upper) hub 54 formed as a boss. The ribs create apertures 53 within the plate forming one axial air inlet into the blower 50. Air flow "B" goes into the inlet during use. The blower also comprises a bottom housing portion ("lower housing") 55. The lower housing is formed from an external annular wall 56 with a concentric internal annular stub wall 57*a* from which radially extends an annular shelf 57*b*. Curved channels 57*c* are formed between the outer and inner annular walls to create an annular airflow stator ring 57 for receiving and slowing airflow from the impeller 27 to create pressure. Ribs 58 extend downwards from the edge of the annular shelf 57*b* and then radially to meet at a central (lower) hub 59. This forms a recessed region ("sub-housing") between the ribs and annular shelf and the lower hub for receiving a motor core 4 comprising a motor (core) stator 16 and rotor 17. The lower housing/lower hub acts as a bottom/lower support for a motor stator 16, and at least a partial support for a bearing, which in turn provides support for a rotor and impeller assembly. The apertures formed between the ribs provide another axial air inlet "A" into the blower. This provides motor cooling also. Two smaller axial inlets (top and bottom) provide a larger effective blade length. The upper housing couples to the top of the external annular wall of the lower housing. This could be by way of bayonets, bumps, snap fits, glue, ultrasonic or friction welding, or any other suitable means.

The motor core comprises the motor stator 16 and rotor 17. The motor stator is supported on the lower hub 59 in the sub-housing. The motor stator comprises a stacked laminated core with a toroidal winding. The rotor comprises an annular or toroidal magnet coupled to a shaft. The lower end of the shaft has an annular rebate with an external diameter commensurate with the inner diameter of the annular magnet for receiving the annular magnet. The shaft is a cylindrical tube in the form of a bearing tube. A bearing, is disposed in the bearing tube at each end. Each bearing race comprises an outer annular bearing race/housing, an inner annular bearing race/housing and ball bearings therebetween. As one non-limiting example, the bearings can have an outside diameter of about 4 mm to 8 mm, an inside diameter of about 1.5 mm to 3 mm and a thickness of about 2 mm to 4 mm. The inner bearing race rotates relative to the outer bearing race. In alternatives, a plane bearing or bushing could be used instead. The shaft is simply supported between the upper housing and the lower housing. Both the upper housing and the lower housing comprise stub axles in the form of compliant and/or resilient protrusions that extend into and couple to the bearing races of the respective bearings at each end of the shaft. Preferably the stub axles are formed from an elastomer (e.g. silicone) or other compliant and/or resilient material, and have a friction fit with the respective bearing races. Alternatively, the stub axles could be solid and/or rigid and are over moulded with a resilient and/or flexible material. Alternatively, the stub axles could be solid. The stub axles may have any one or more of the features described above in respect of the first embodiment.

The impeller can be coupled onto (e.g. press fit) or integrally formed with the shaft. The shaft can be of similar diameter to the shaft in traditional topologies, which allows for robust mechanical coupling of the impeller. Because the bearings are fitted on the inside of the shaft, the diameter of the shaft is not dictated by the inner diameter of the bearings. The outer diameter of the shaft can then be a suitable size to allow for a robust impeller coupling, e.g. about 5 mm, or alternatively from about 3 mm to about 5 mm. A larger diameter shaft can still be used without dictating the bearing diameter size (leading to undesirably high bearing speeds), because the bearings are internal to the shaft, the size of the bearing (e.g. the diameter size) can be selected based on acceptable bearing speed. The impeller is shown in FIG. 2. The impeller is also shown in FIGS. 5 and 6 in more detail. Similarly, the magnet/rotor 17*a*/17 is pressed onto the shaft. Similar advantages apply here, where the shaft can be a suitable size to allow for robust coupling. The impeller comprises a hub portion and flat forward swept (full-length) blades, which radially extend from and connect to the hub portion. (Alternatively, the blades could be backward swept or radial). Each blade comprises a vertical flat portion extending from the hub. An annular rib/ring 7 is formed into the blades 6 and extends between them to provide rigidity at the perimeter of the blades. The ring curves towards the outlet 7*a* to provide rigidity to the blades and also direct airflow through the airflow stator to be described later. A plurality of short stub (partial-length) blades 8 (also termed "splitter blades") that extend part-way to the hub are interspaced between the full length blades 6. The annular rib is also formed into and extends between the blades, thus supporting them. The stub blades provide additional pressure, without the requirement for material to extend to the hub which reduces air space at the hub. Reducing airspace at hub reduces the maximum flow capability of the blower 10. If the number of blades is too high (and therefore there is too little air space at the hub due to too many blades), inlet flow is occluded, which restricts the outlet airflow of the blower. The impellor may be in accordance with the embodiments illustrated in FIGS. 5 and 6 and may have any one or more of the features described above in respect of the first embodiment.

This embodiment has the same advantages as described for the previous embodiment. It also has the further advantage of a dual axial inlet, providing for a less restrictive air inlet. It also provides motor cooling.

THIRD EMBODIMENT

Figure 4:
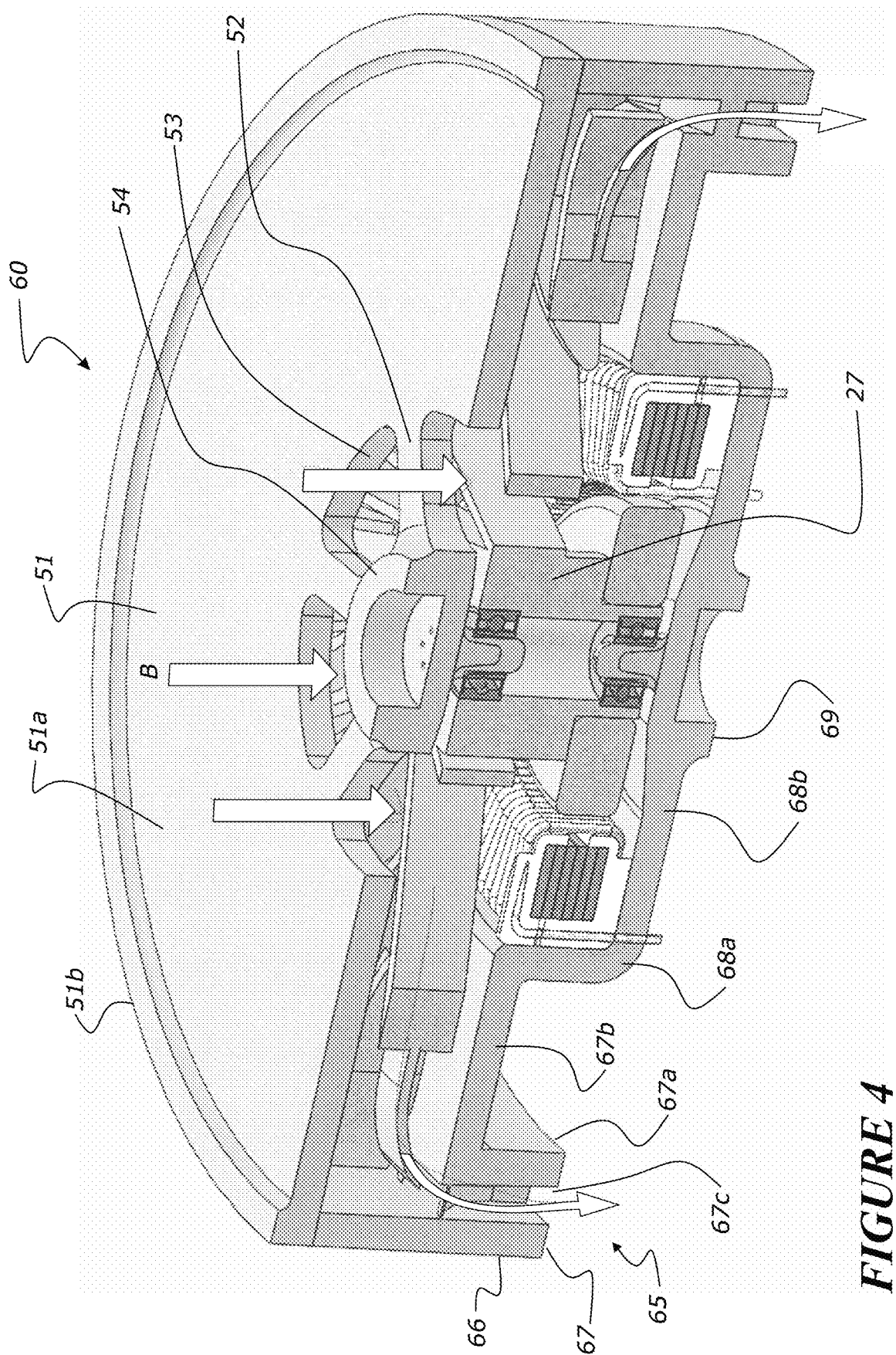
FIG. 4 shows a cross-sectional perspective view of a low-profile blower, with an axial inlet and an axial output according to a third embodiment.

FIG. 4 shows yet another embodiment 60 of single stage axial inlet/axial outlet blower. This embodiment is similar to the previous embodiment, however, there is one axial inlet at the top of the motor.

The motor comprises a top housing portion ("upper housing") 51 comprising a plate 51*a* with an annular rim 51*b*. At a central portion of the plate, a plurality of ribs 52 extend into a central upper hub 54 formed as a boss. The ribs create apertures 53 within the plate 51*a* forming one axial air inlet into the blower 60. Air flow "B" goes into the inlet during use. The blower also comprises a bottom housing portion ("lower housing") 65. The lower housing is formed from an external annular wall 66 with a concentric internal annular stub wall 67*a* from which radially extends an annular shelf 67*b*. Curved channels 67*c* are formed between the outer and inner annular walls to create an annular airflow stator ring 67 for receiving and slowing airflow from the impeller 27 to create pressure. An annular wall 68*a* extends downwards from the edge of the annular shelf and then a floor 68*b* extends radially to meet at a central lower hub 69. This forms a recessed region ("sub-housing") 68 between the wall and annular shelf and the lower hub for receiving a motor core comprising the motor stator and rotor. The lower housing/lower hub acts as a bottom/lower support for a motor stator, and at least a partial support a bearing which in turn provides support for a rotor and impeller assembly. The upper housing couples to the top of the external annular wall of the lower housing. This could be by way of bayonets, bumps, snap fits, glue, ultrasonic or friction welding, or any other suitable means.

The motor core comprises the motor stator and rotor. The motor stator is supported on the lower hub in the sub-housing. The motor stator comprises an annular stacked laminated core with a toroidal winding. The rotor comprises an annular or toroidal magnet coupled to a shaft. The lower end of the shaft has an annular rebate with an external diameter commensurate with the inner diameter of the annular magnet for receiving the annular magnet. The shaft is a cylindrical tube in the form of a bearing tube. A bearing, is disposed in the bearing tube at each end. Each bearing race comprises an outer annular bearing race/housing, an inner annular bearing race/housing and bearings therebetween. As one non-limiting example, the bearings can have an outside diameter of about 4 mm to 8 mm, an inside diameter of about 1.5 mm to 3 mm and a thickness of about 2 mm to 4 mm. The inner bearing race rotates relative to the outer bearing race. In alternatives, a plane bearing or bushing could be used instead. The shaft is simply supported between the upper housing and the lower housing. Both the upper housing and the lower housing comprise stub axles in the form of compliant and/or resilient protrusions that extend into and couple to the bearing races of the respective bearings at each end of the shaft. Preferably the stub axles are formed from an elastomer (e.g. silicone) or other compliant and/or resilient material, and have a friction fit with the respective bearing races. Alternatively, the stub axles are solid and/or rigid and are over moulded with a resilient and/or flexible material. Alternatively, the stub axles could be solid. The stub axles may have any one or more of the features described above in respect of the first embodiment.

The impeller can be coupled onto or integrally formed with the shaft. The shaft can be of similar diameter to the shaft in traditional topologies, which allows for robust mechanical coupling of the impeller. Because the bearings are fitted on the inside of the shaft, the diameter of the shaft is not dictated by the inner diameter of the bearings. The outer diameter of the shaft can then be a suitable size to allow for a robust impeller coupling, e.g. about 5 mm, or alternatively from about 3 mm to about 5 mm A larger diameter shaft can still be used without dictating the bearing diameter size (leading to undesirably high bearing speeds), because the bearings are internal to the shaft, the size of the bearing (e.g. the diameter size) can be selected based on acceptable bearing speed. The impeller is shown in FIG. 2. The impeller is also shown in FIGS. 5 and 6 in more detail. Similarly, the magnet/rotor 17a/17 is pressed into the shaft. Similar advantages apply here, where the shaft can be a suitable size to allow for robust coupling. The impeller comprises a hub portion and flat forward swept (full-length) blades, which radially extend from and connect to the hub portion. (Alternatively, the blades could be backward swept or radial). Each blade comprises a vertical flat portion extending from the hub. An annular rib/ring 7 is formed into the blades 6 and extends between them to provide rigidity at the perimeter of the blades. The ring curves towards the outlet 7a to provide rigidity to the blades and also direct airflow through the air flow stator to be described later. A plurality of short stub (partial-length) blades 8 (also termed "splitter blades") that extend part-way to the hub are interspaced between the full length blades 6. The annual rib is also formed into and extends between the blades, thus supporting them. The stub blades provide additional pressure, without the requirement for material to extend to the hub which reduces air space at the hub. Reducing airspace at hub reduces the maximum flow capability of the blower 10. If the number of blades is too high (and therefore there is too little air space at the hub due to too many blades), inlet flow is occluded, which restricts the outlet airflow of the blower. The impellor may be in accordance with the embodiments illustrated in FIGS. 5 and 6 and may have any one or more of the features described above in respect of the first embodiment.

This embodiment has the same advantages as described for the previous embodiment.

Another advantage of the resilient stub axles described in the above embodiments is that they accommodate misalignment of the connection between the shaft and the bearings and enable pre-loading of the bearings.

In the embodiments described above, the shaft is hollow to allow the bearings to sit within the shaft at each end. In other embodiments, the shaft might only be partially hollow, but with sufficient space for the bearings to sit inside the shaft. For example, the shaft could have recesses in each end for seating the bearings.

Figure 7:
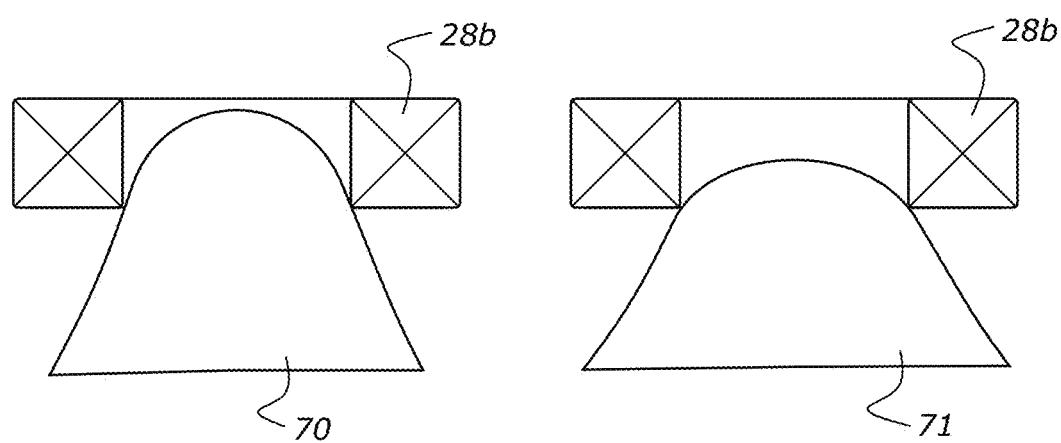
FIG. 7 shows two alternative stub axle and bearing arrangements.

Referring to FIG. 7, in another alternative, the stub axles of the embodiments above might not extend through the bearings. Rather each stub axle might only partially extend into (e.g. see stub axle 70), or just contact (e.g. see stub axle 71) the bearing. These arrangements still provide sufficient support and allow for rotation.

FOURTH EMBODIMENT

Figure 8:
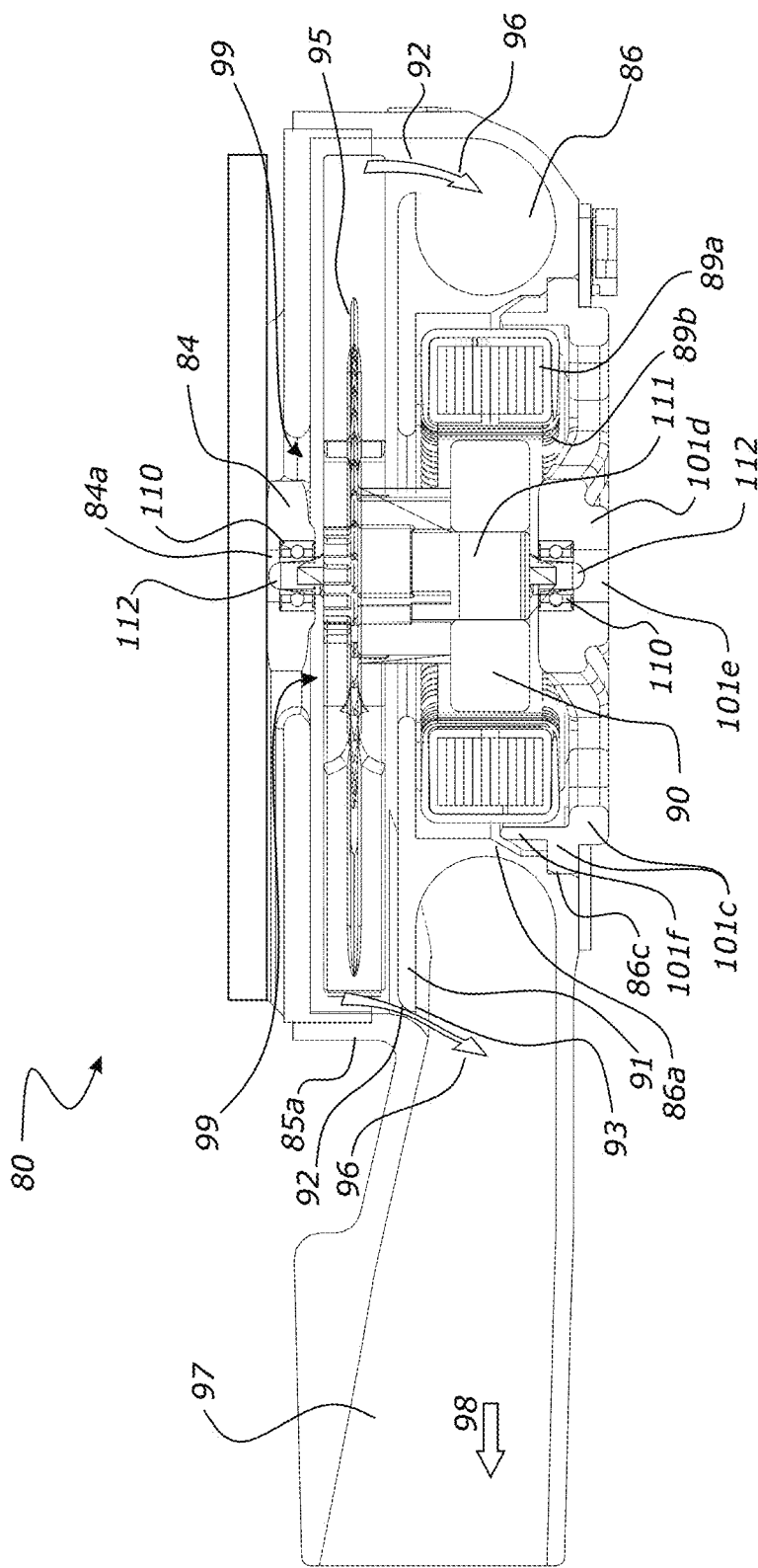
FIGS. 8 to 11 show cross-sectional and perspective view of a low-profile blower, with an axial inlet and radial outlet according to a fourth embodiment.
Figure 9:
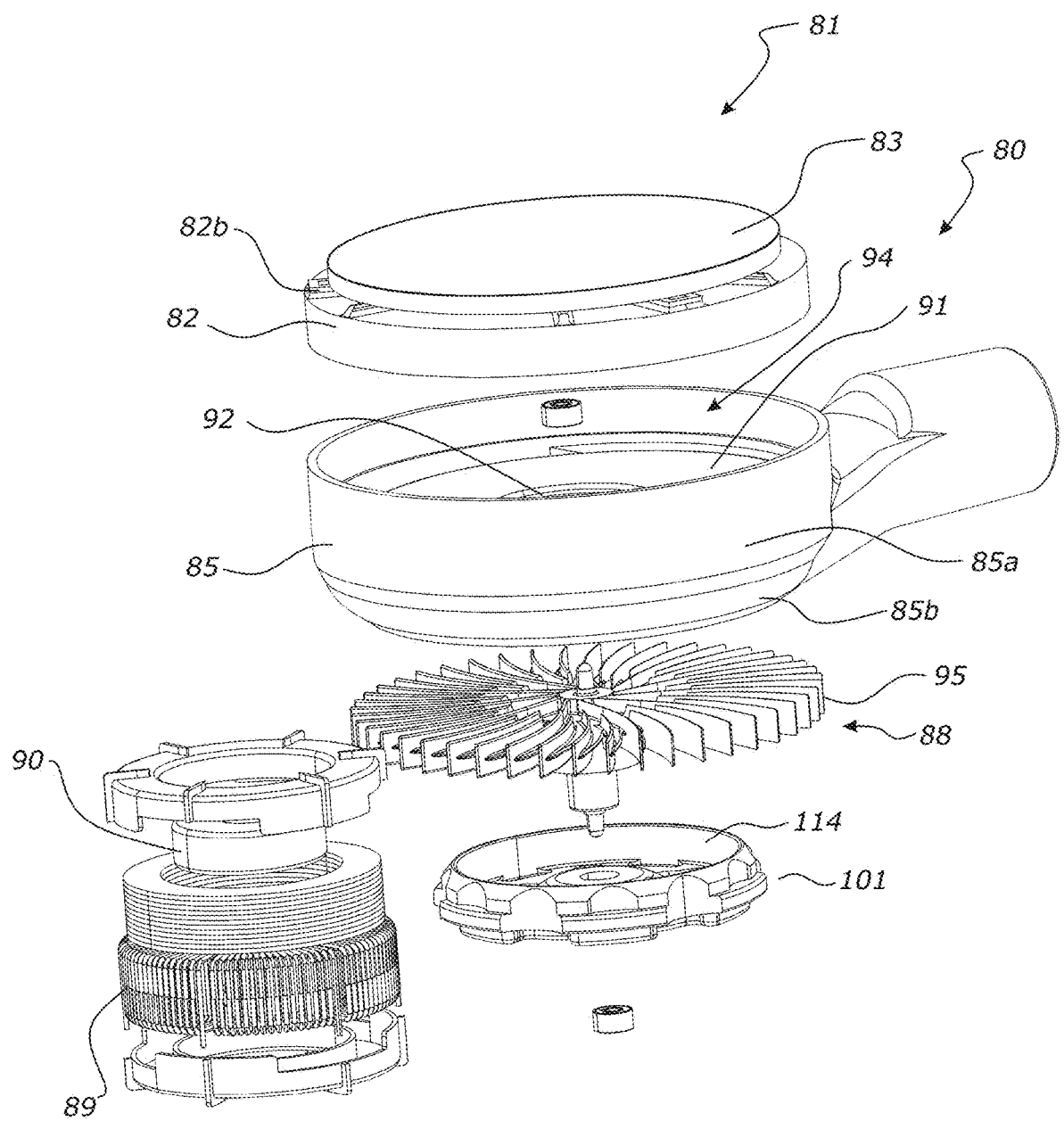
Figure 10:
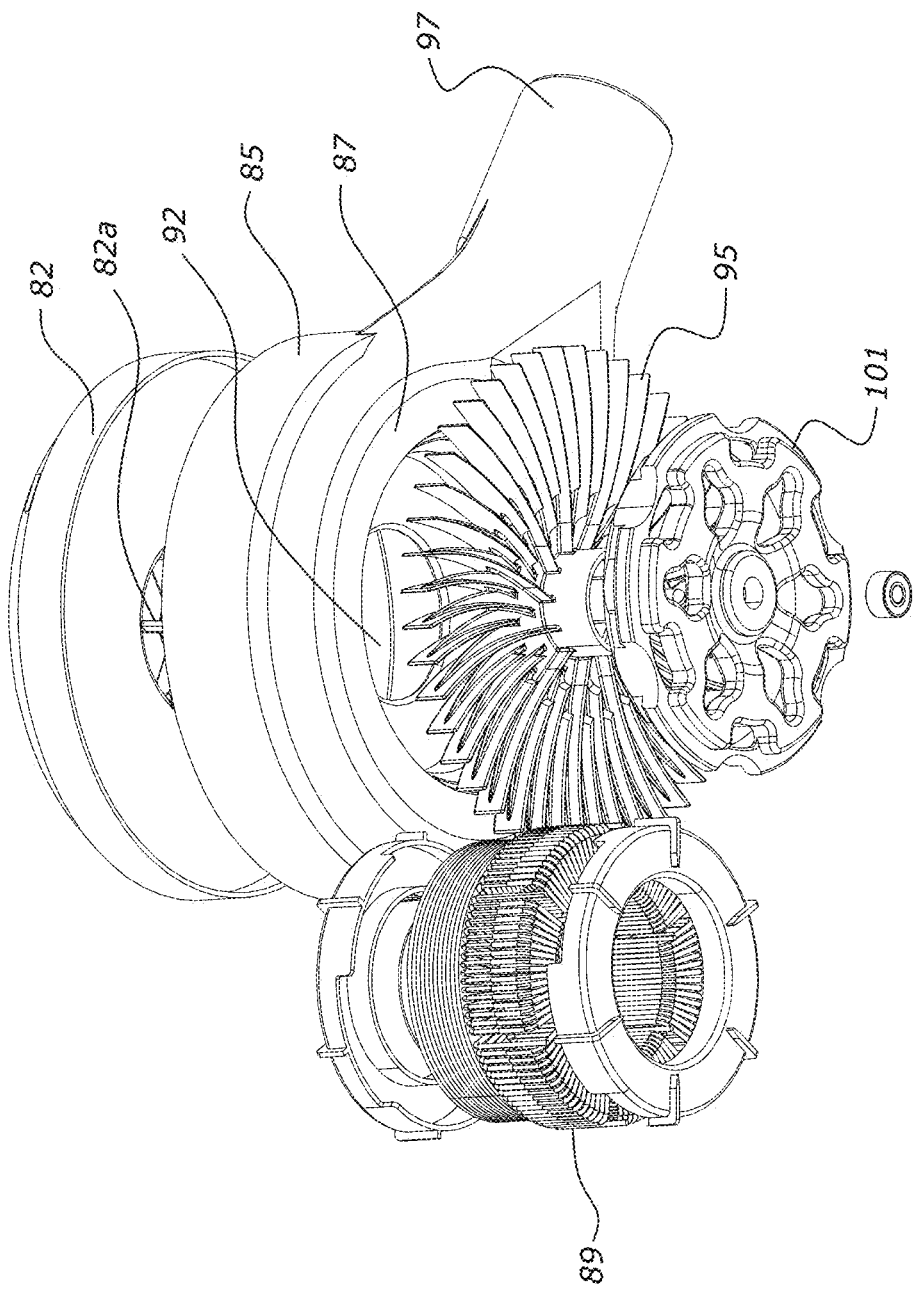

FIGS. 8 to 10 show yet another embodiment 80 of a blower, this one being a single stage axial inlet/radial outlet blower.

The blower 80 comprises a bottom housing portion ("lower housing") 85. The lower housing is formed as a generally round body with a cylindrical side 85a and a toroidal base portion 85b forming part of an annular collector 86 (for collecting flow from the impeller) and an inner motor region 87 (see FIG. 10) concentric within the annular collector centre. The inner motor region is formed as a recess within the lower housing. An inner wall 86a of the collector curves upwards to form the inner motor region 87. The inner motor region ("sub-housing") 87 is for receiving a motor core 88 assembly comprising the motor (core) stator 89 and rotor 90. A central plate 91 with a central aperture is supported on the inner collector wall 86a. The plate is dimensioned with an annular gap 92 between the plate perimeter 93 and the inner cylindrical side wall 85a to define a top impeller region 94 in the housing body 85. The annular gap 92 provides an air flow path 96 from an impeller 95 to the collector 86. A radial outlet 97 conduit extends from the collector 86 for provision of a flow of air 98 from the impeller.

The blower 80 comprises a top housing portion ("upper housing") 81 comprising a plate 82 with a central air inlet aperture 82a (see FIG. 10, 11), and ribs 82b extending radially across the plate across the central air inlet aperture 82a to a hub. The ribs 82b are shown exposed in FIG. 11. Alternatively, the ribs 82b can be skewed 200 at the central hub 200, as shown in the alternative embodiment in FIG. 13A. The skewing reduces the interaction with the blades of the impeller. In the particular embodiment illustrated in FIG. 13, each of the ribs comprise a radial portion and a skewed portion. Each skewed portion extends along an axis that is transverse to a longitudinal axis of its respective radial portion. Each radial portion extends from a periphery of the plate to an outer edge of the central hub and each skewed portion extends from the outer edge of the central connecting portion which connects to all of the other skewed portions. An opening is formed between each adjacent skewed portion for air flow into the motor. In other embodiments, the skewed portions of each of the ribs 82 could be curved at the central hub region to minimise interaction with the impeller blades. FIGS. 11 and 13A-13C show 5 ribs, however, it will be appreciated there may be various numbers of ribs provided for example 3, 5 or 9 ribs. It may be advantageous to have an odd number of ribs to ensure the ribs provide a stable support base for the hood 83. As can be seen in FIGS. 11 and 13A-13C the ribs 82*b* may be arranged in an equiangular manner. The upper housing 81 may further comprise engagement features configured to orient and/or attach the upper housing 81 to the hood 83.

Figure 11:
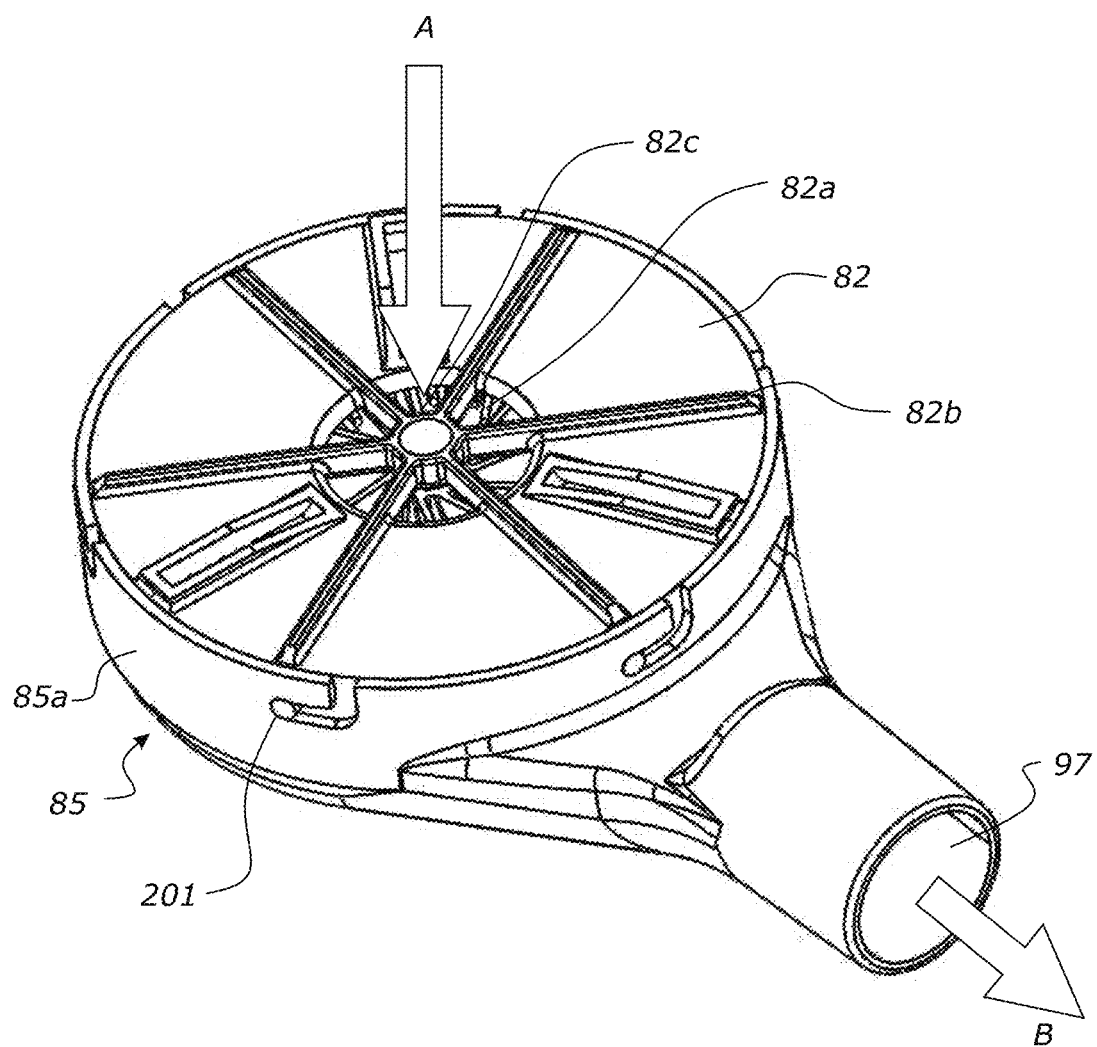

As can be seen from FIG. 11, the plate 82 can be coupled to the cylindrical side 85*a* with a bayonet coupling 201, although friction fit or other couplings can be used. A hood 83 sits on the ribs. The ribs 82*b* set the hood 83 away from the plate to allow an air path 99 into the air inlet aperture 82*a* so air can reach the impeller 95. Air flow 9 goes into the inlet during use. The ribs 82*b* also extend to and support a central top hub 84 within the central aperture 82*a*, the top hub also comprising a central aperture 84*a*.

A motor assembly 88 is assembled into the inner motor region 87. A motor stator support 101 is arranged into an annular opening of the motor region 87 to form a base of the motor 88 sub-housing. The motor stator support 101 has a profiled annular perimeter 101*a* that sits in a corresponding annular rebate/shelf 86*c* in the inner collector wall 86*a*. The motor stator support 101 also has a plurality of ribs 101*b* extending radially from an annular perimeter 101*c* to a bottom hub 101*d* with a central aperture 101*e* housing a bearing race 110. As previously described top hub 84 is supported from the ribs of the hood, also with a central aperture 84*a* housing a bearing race 110. The bearing races can be as previously described in the previous embodiments. In alternatives, a plane bearing or bushing could be used instead. A shaft 111 is supported between the top 84 and bottom hubs 101*d* within the respective bearing races 110 and extends from the top hub 84 through the central aperture 92 of the central plate 91. The shaft is solid, although alternatively could be hollow, or partially hollow, as will be described later. Stub axles 112 on either end of the shaft 111 support the shaft in the respective bearings 110. The annular perimeter of the motor stator support also has a cylindrical side wall 101*f* forming a region 114 for concentrically supporting an annular/toroidal motor stator 89 comprising an annular stacked laminated core 89*a* with a toroidal winding 89*b*. An annular/toroidal magnet 90 is supported concentrically on the shaft 111 and resides concentrically within the motor stator/motor stator region. An impeller 95 is supported on the shaft 111 and housed within the impeller region 94 of the body 85. The impeller 95 can be any of those previously described. The impeller can be coupled onto or integrally formed with the shaft 111. The shaft 111 can be of similar diameter to the shaft in traditional topologies, which allows for robust mechanical coupling of the impeller.

In operation, the impeller spins and draws air through the central aperture and passes it down around the annular gap into the volume and out the radial outlet.

This embodiment has the same advantages as described for the previous embodiments.

The shaft 111/stub axle 112/bearing 110 arrangement of this embodiment is the reverse arrangement of the previous embodiments. Rather than the bearings 110 being supported in the shaft 111, and the stub axles 112 being supported in the upper/lower housing or hubs, in this embodiment the stub axles 112 are on the shaft 111 and the bearings 110 are in the top 84 and bottom 101 hubs.

Each of the stub axles extend to a distal end from respective upper and lower ends of the shaft. The stub axles extend away from each other. Each of the stub axles are substantially cylindrically shaped. In other embodiments, one or both of the stub axles taper or decrease in diameter as they extend away from the respective upper and lower ends of the shaft. The distal end of each stub axle is rounded. However, in other embodiments, the distal end of one or both of the stub axles is substantially flat. Each stub axle also comprises a shoulder that is formed by a flange or stepped portion. In other embodiments, the shoulder formed by a taper in the stub axle. The shoulder is located at or near a proximal end of each stub axle to the shaft. Upper and lower bearings engage the shoulder or respective stub axles to limit axial movement of the bearing arrangement towards the shaft. Each of the top 84 and bottom 101 hubs has a shoulder in an opposed relationship to each respective stub axle shoulder. Each hub shoulder is formed as a recess or stepped portion in an internal surface of the hub. In other embodiments, the hub shoulder is formed by a taper in the internal surface of the hub. The upper and lower bearings also engage respective hub shoulders so that they are gripped between a shoulder on a respective hub and a shoulder on a respective stub axle.

In all embodiments, the arrangement is such that a bearing and stub axle arrangement couples the shaft to upper/top and lower/bottom supports of the blower. The bearings and shaft can otherwise have similar configurations (although in this embodiment the shaft need not be hollow), and as such this arrangement still provides the same benefits as the previous embodiments. The shaft can be of similar diameter to the shaft in traditional topologies, which allows for robust mechanical coupling of the impeller. But, because the stub axles can be thinner than the shaft and extend into the bearings, the diameter of the shaft is not dictated by the inner diameter of the bearings. The outer diameter of the shaft can then be a suitable size to allow for a robust impeller coupling, e.g. about 5 mm, or alternatively from about 3 mm to about 5 mm A larger diameter shaft can still be used without dictating the bearing diameter size, because the bearings are off the shaft. The size of the bearing (e.g. the diameter size) can therefore be selected based on acceptable bearing speed. Similarly, the magnet/rotor 17/17*a* is pressed into the shaft. Similar advantages apply here, where the shaft can be a suitable size to allow for robust coupling.

The embodiments above show some examples of the shaft, stub axle and bearing arrangement that provide the advantages of the present invention. However, these embodiments are not exhaustive. More generally, it will be appreciated that other embodiments are also possible, with any combination of the following configurations:

bearings in the shaft, or alternatively bearings on the top/bottom support stub axles in the top/bottom support, or alternatively stub axles on the shaft hollow, partially hollow, or solid shaft.

Figure 12A:
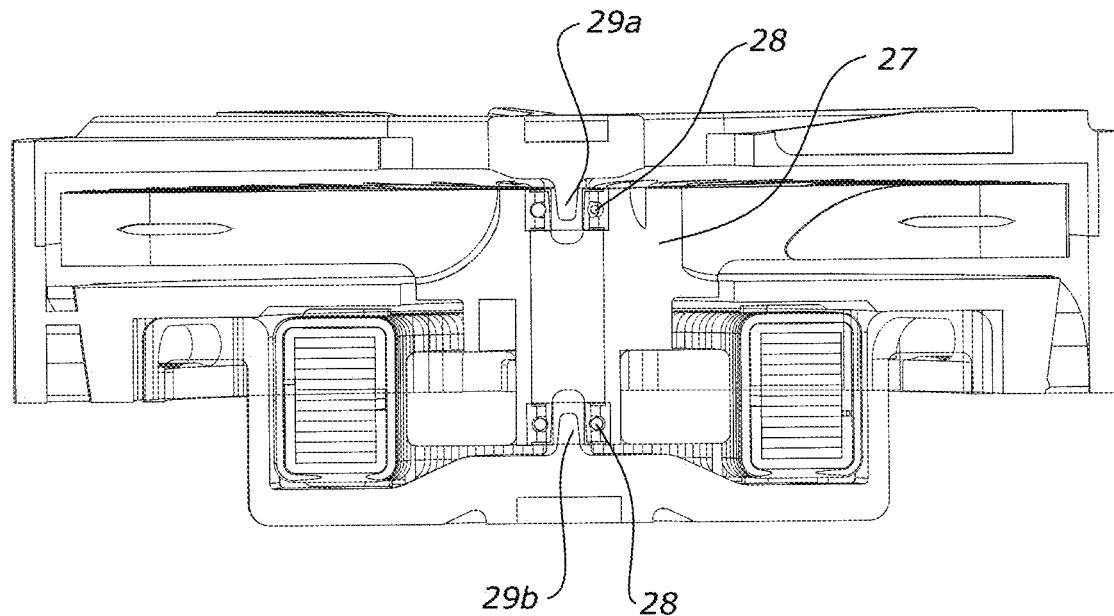
FIGS. 12A to 12C show various configurations of the stub axle, bearings and shaft that could be used in variations.

As an example, and referring to FIG. 12A, in some embodiments, the blower has a hollow shaft 27, bearings 28 at either end of the shaft, and stub axles 29*a*, 29*b* on the top/bottom support.

Figure 12B:
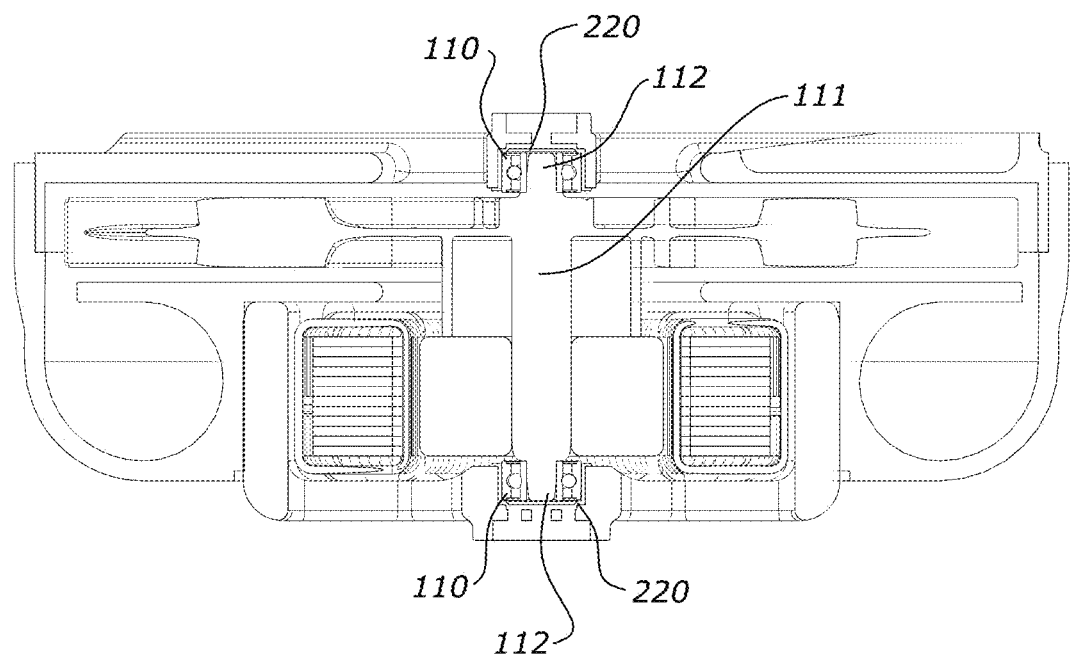

As another example, and referring to FIG. 12B, in some embodiments, the blower has a solid shaft 111, stub axles 112 on either end of the shaft 111, and bearings 110 on the top/bottom support. As illustrated in FIG. 12B, the stub axles 29a, 29b in the impeller are rigid and the top/bottom supports have a resilient "cup" 220 to accept the bearing. The resilient material of the cup 220 is thin, and is just visible in the cross-section view. Alternatively, as previously described, the stub axles 29a, 29b are made of resilient material.

Figure 12C:
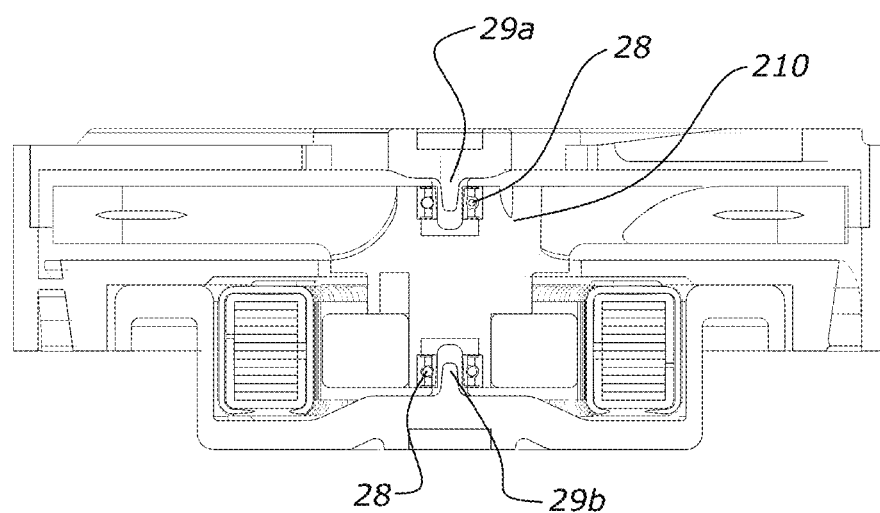

As another example, and referring to FIG. 12C, in some embodiments, the blower has a partially hollow shaft 210, bearings 28 at either end of the shaft, and stub axles 29a, 29b on the top/bottom support. In these embodiments, the shaft has recesses formed in each end of the shaft. The bearings and stub axles are at least partially received within respective recesses of the shaft.

Figure 13A:
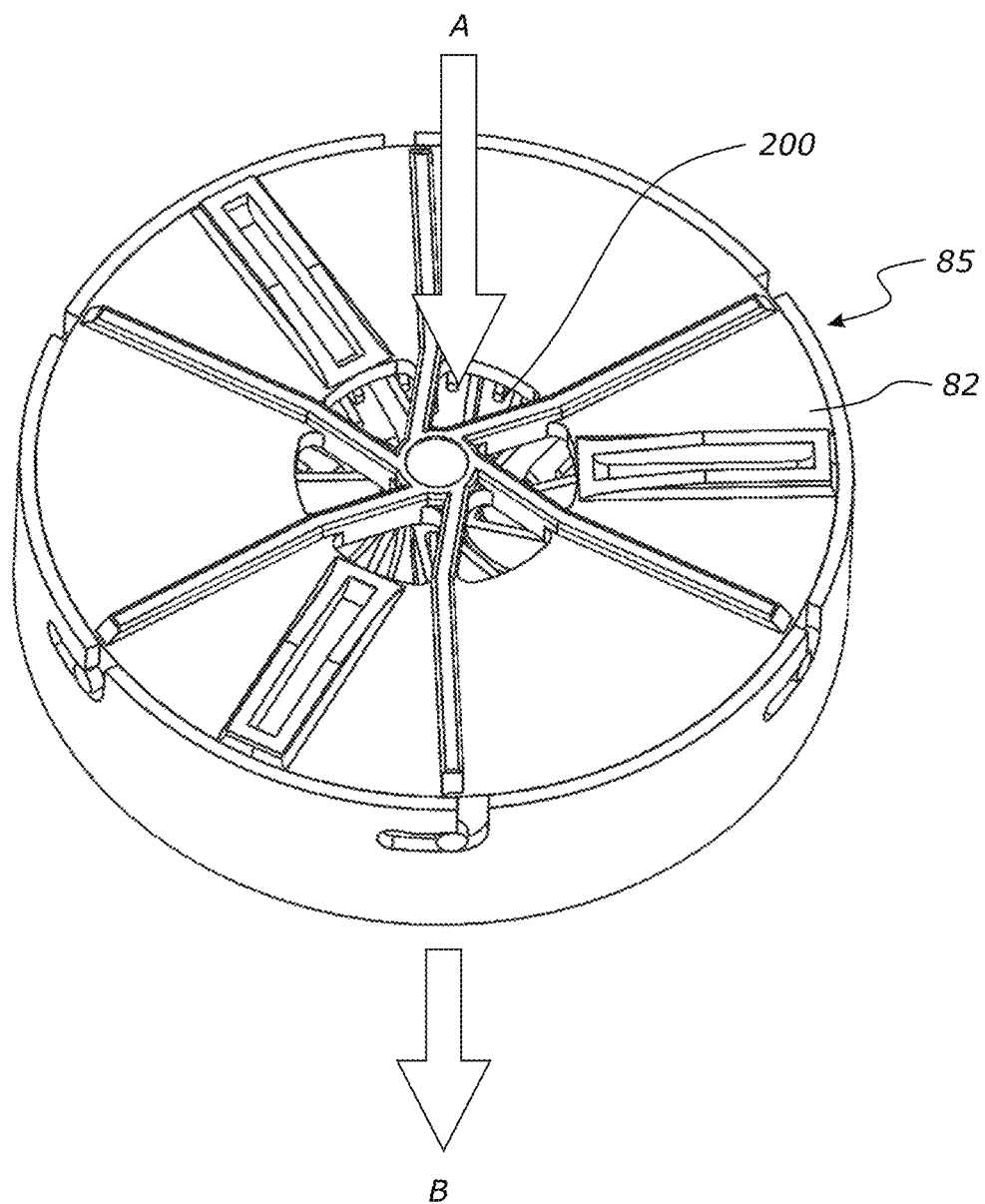
FIGS. 13A to 13C show various inlet/outlet configurations of the blower that could be used in variations.
Figure 13B:
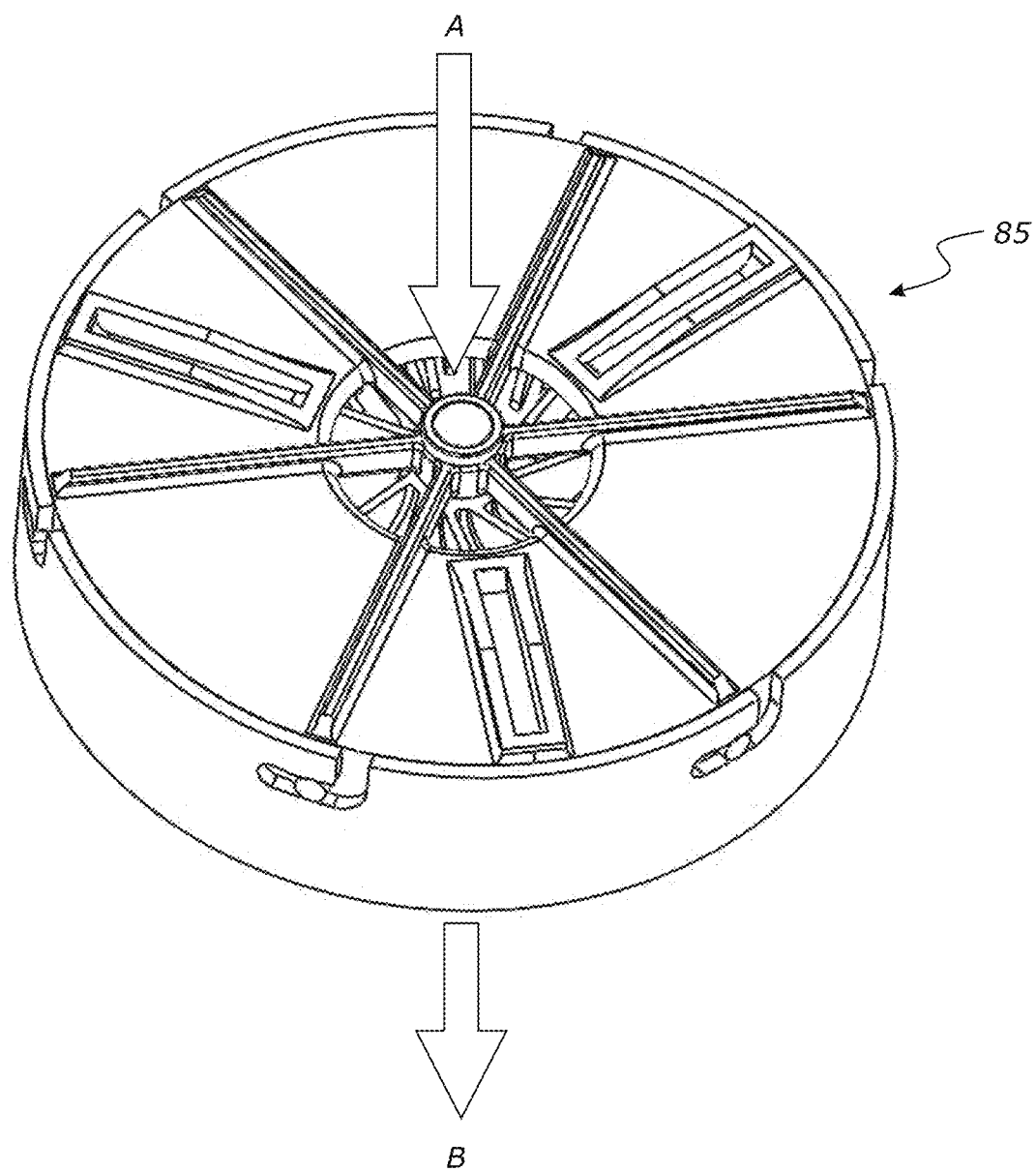
Figure 13C:
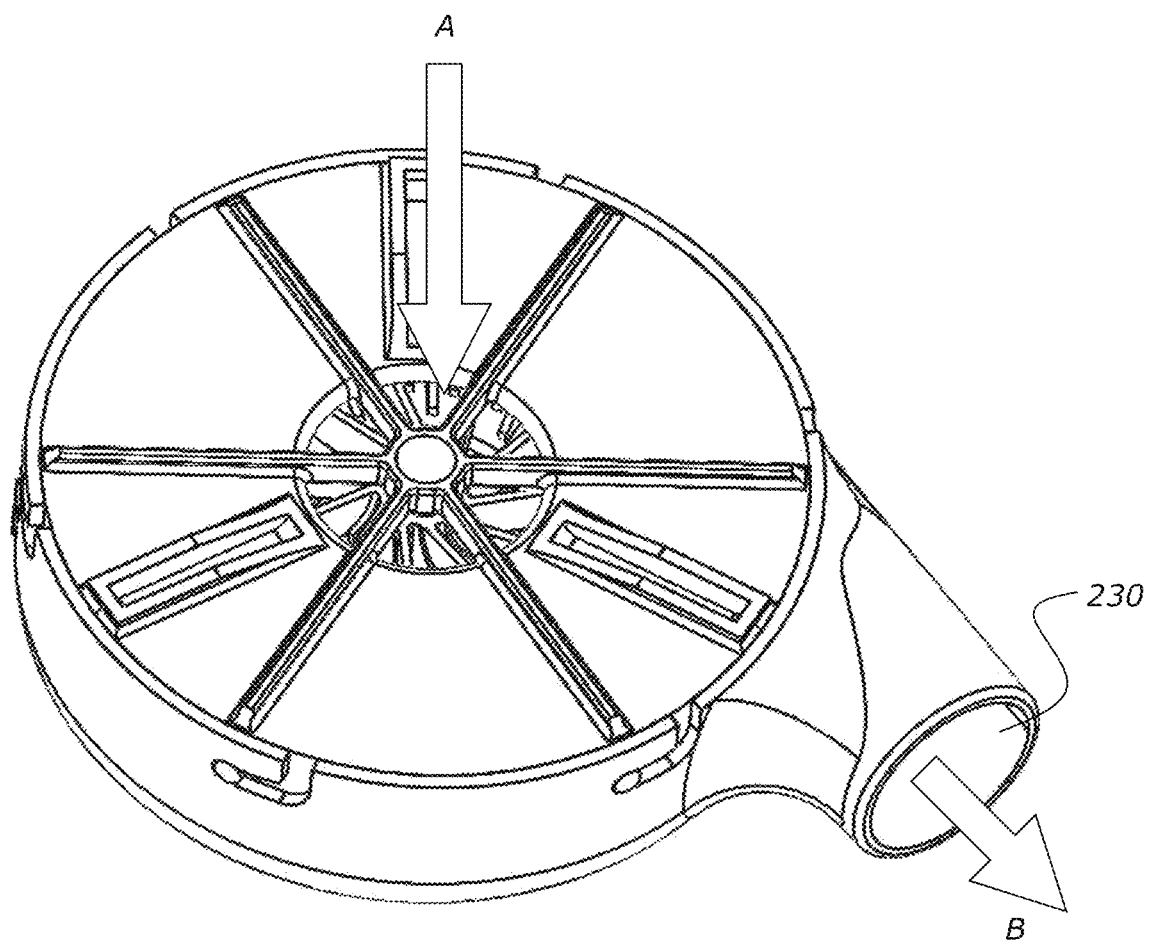

The embodiments above show various configurations of inlet/outlet topologies. Various combinations of inlet and outlet topologies could be incorporated into any of the above described embodiments. For example, in some embodiments, as shown in FIGS. 13A, 13B, the blower could have an axial inlet A/axial outlet B topology (the ribs 82b being different in each case). In other embodiments, as shown in FIG. 11, the blower could have an axial inlet A/radial outlet B/97 topology. In other embodiments, as shown in FIG. 13C, the blower could have an axial inlet A/tangential outlet C/230 topology.

Other topologies of motors are possible, and those described are exemplary only. For example, a brushed or brushless DC motor, AC motor, inductance motor or variable reluctance motor could be used. The rotor and motor stator could take other forms to that described.

The embodiments described have a number of advantages. They provide a reduced footprint blower, both in profile and/or plan. A smaller foot print allows for a smaller housing. One reason for the smaller foot print is that the airflow stator ring allows a volute to be omitted, reducing overall diameter of the blower, and also increasing the ratio of blade length to housing diameter (that is, the space for blade length is not reduced due to the presence of a volute allowing the blade length to use more of the available footprint diameter than a housing with a volute).

The embodiments also allow for the use of a smaller impeller (that is, smaller in diameter thickness and/all weight). This in turn leads to a smaller/lighter blower and/or a blower with a lower inertia. A smaller/lighter topology enables the blower to be used in portable, miniaturised and/or head or mask mounted CPAP, high flow therapy or other breathing apparatus.

As an example, the impeller might have a diameter of about 47 mm inside an about 48 mm diameter ring provide a ratio of blade length to housing diameter of 98%. Another example is about 18 mm blades in an about 20 mm radius housing for a 90% ratio. These are just illustrative examples and other diameters are possible. A typical envelope/footprint of the blower could be:

Diameter: <=about 53 mm
Height: <=about 21 mm
Weight: <=about 50 grams, or <=about 47 grams (for example 27 grams)
Optionally the impeller has:
a thickness of less than or equal to about 3 mm
a diameter of less than or equal to about 48 mm, or more preferably 48.4 mm
a weight of less than or equal to about 3 grams Other dimensions will become apparent upon reading this description. Maximising the blade to housing ratio is preferred.

Small impellers of these dimensions have not been suitable for use in the applications described above. This is because, when operated at the usual speeds (revolutions per minute), the air flow characteristics are insufficient to provide required therapy (for example, the flow rate and/or pressure generated by smaller impellers of this nature are not sufficient). Further, it has not been possible to run these impellers are high speeds to create the required flow rates and/or pressures, because those speeds create a number of disadvantages. For example, with increased speed, the bearings operate at a higher speed and/or temperature. This requires the use of special bearings, such as ceramic, air or fluid bearings, which are more expensive. Smaller diameter bearing races and bearings need to be used to reduce the speed of the bearings. This leads to a necessary drop in the shaft diameter, so that the shaft can still go through the centre of the bearing race. When using a smaller diameter shaft, it is much more difficult to attach the impeller and/or rotor magnet, for example through integral design or a friction fit. The manufacturing tolerances are too precise for this to be done in a viable manner. Therefore, accommodating a smaller impeller up to now has been impracticable. Another alternative is to use a blower with multiple impeller stages, however that is more expensive, larger and is more difficult to manufacture.

The present embodiments overcome these issues and allows for the use of a smaller impeller in a single-stage blower. The shaft that is used is hollow, or at least partially hollow. Bearings are fitted to the inside of the shaft. This allows for two things. First it allows for the shaft diameter to be of the same or similar size as previously, so that an impeller and/or rotor (or magnet) can be integrated into or fitted to a shaft in the usual manner; and second because the bearings are disposed internally, it allows for smaller diameter bearings (while still having the same is diameter shaft) to be used. This then allows the impeller to be spun at higher speeds to create the required flow rate and/or pressure with a smaller diameter impeller. But, despite the impeller/shaft being run at higher speeds, the smaller diameter bearings run at a lower circumferential speed (or a higher angular rate) than would larger diameter bearings traditionally used, which avoids the problems with higher speeds mentioned above. The stub axles therefore allow for connection to the internal races of the bearings, and the compliance/resilience of the stub axles allow for compliance when the shaft spins. The arrangement also reduces or eliminates eddy currents in the shaft and/or bearings. The eddy currents can degrade the bearings.

In addition, the stub blades and increased air inlet numbers and/or size allow for more pressure to be generated from a smaller blade length.

The axial outlet eliminates the need for a tangential outlet duct, which can increase the blower footprint.

The arrangement also allows for a single stage axial input/axial output blower, which provides for a reduced footprint or lower (low) profile. The embodiment described does not have a volute which reduces the size also. The airflow stator ring creates static pressure. The axial airflow inlet allows for motor stator cooling.

The invention claimed is:

1. A blower for a breathing apparatus comprising:
a housing comprising:
a bottom support forming a bottom portion of the housing, and
a top support forming a top portion of the housing;
a motor core comprising a stator and a rotor;
an impeller coupled to the motor core via a rotatable shaft;
wherein a first end of the rotatable shaft is rotatably coupled to the top support via a first stub axle and first bearing arrangement and a second end of the rotatable shaft is rotatably coupled to the bottom support via a second stub axle and second bearing arrangement;

wherein the rotatable shaft is at least partially hollow; and wherein the first stub axle extends from the top support and the second stub axle extends from the bottom support such that the first stub axle and the second stub axle extends into the rotatable shaft.

2. The blower of claim 1, wherein at least one of the first bearing arrangement and the second bearing arrangement are located within the rotatable shaft that is at least partially hollow.

3. The blower of claim 1, wherein the housing further comprises an annular collector configured to collect flow from the impeller and an inner motor region within the annular collector, and wherein the motor core is located within the inner motor region.

4. The blower of claim 3, wherein the housing further comprises an inner motor region, wherein the inner motor region is concentric with the annular collector.

5. The blower of claim 4, wherein the inner motor region is formed as a recess within the housing.

6. The blower of claim 4, wherein the inner motor region is formed by an inner wall of the annular collector.

7. The blower of claim 5, wherein the motor core is positioned within the recess of the housing.

8. The blower of claim 1, wherein the rotatable shaft is configured to rotate relative to the top support and the bottom support.

9. The blower of claim 1, wherein the housing further comprises an annular airflow stator ring.

10. The blower of claim 1, wherein at least one of the first stub axle and the second stub axle further comprises a shoulder that is formed by at least one of a flange, stepped portion, or a taper.

11. The blower of claim 1, wherein each of the first bearing arrangement and the second bearing arrangement comprise an inner race and an outer race, and wherein each of the first stub axle and the second stub axle couples to a respective inner race.

12. The blower of claim 11, wherein at least one of the first stub axle and the second stub axle tapers within the respective inner race.

13. The blower of claim 1, wherein the housing comprises a lower housing with a region for the motor core and one or more apertures for axially receiving air from an inlet.

14. The blower of claim 1, wherein the blower is a single stage blower.

15. The blower of claim 1, wherein a ratio of an impeller diameter to a diameter of the housing is at least about 90%.

16. The blower of claim 1, wherein a maximum diameter of the rotatable shaft is independent of a diameter of a bearing in the first bearing arrangement or the second bearing arrangement.

17. The blower of claim 1, wherein a maximum diameter of the rotatable shaft is greater than a diameter of a bearing in the first bearing arrangement or the second bearing arrangement.

18. The blower of claim 1, wherein the rotatable shaft is completely hollow.

19. The blower of claim 1, wherein the housing further comprises:

an annular collector for collecting flow from the impeller;

an inner motor region within the annular collector, the inner motor region formed as a recess within the housing; and wherein the motor core is located within the inner motor region.

* * * * *